(12) United States Patent
Rao

(10) Patent No.: US 11,484,726 B2
(45) Date of Patent: Nov. 1, 2022

(54) SYSTEM AND METHOD FOR PERFORMING TRANSLUMBOSACRAL NEUROMODULATION THERAPY IN A SUBJECT

(71) Applicant: Satish S C Rao, Martinez, GA (US)

(72) Inventor: Satish S C Rao, Martinez, GA (US)

(*) Notice: Subject to any disclaimer, the term of this patent is extended or adjusted under 35 U.S.C. 154(b) by 385 days.

(21) Appl. No.: 16/869,487

(22) Filed: May 7, 2020

(65) Prior Publication Data

US 2020/0353275 A1 Nov. 12, 2020

Related U.S. Application Data

(60) Provisional application No. 62/844,621, filed on May 7, 2019.

(51) Int. Cl.
*A61N 2/02* (2006.01)
*A61B 5/00* (2006.01)
*A61B 5/296* (2021.01)
*A61B 5/392* (2021.01)

(52) U.S. Cl.
CPC ............... *A61N 2/02* (2013.01); *A61B 5/296* (2021.01); *A61B 5/392* (2021.01); *A61B 5/4836* (2013.01); *A61B 5/6873* (2013.01)

(58) Field of Classification Search
CPC .................................. A61N 2/02; A61N 2/004
See application file for complete search history.

(56) References Cited

U.S. PATENT DOCUMENTS

| 9,393,409 | B2 | 7/2016 | Edgerton et al. |
| 10,335,596 | B2 | 7/2019 | Yakovlev et al. |
| 2006/0122660 | A1 | 6/2006 | Boveja et al. |
| 2019/0255325 | A1 | 8/2019 | John et al. |

FOREIGN PATENT DOCUMENTS

WO WO2011158018 A1 12/2011

OTHER PUBLICATIONS

Xiang X, Sharma A, Patcharatrakul T, Parr R, Hall P, Hamdy S, Rao SSC. Translumbar and Transsacral Magnetic Stimulation Thrapy for the Treatment of Fecal Incontinence: Interim Analysis of a Dose Ranging Study. Gastroenterology 2018. 154; S540.

(Continued)

*Primary Examiner* — John P Lacyk

(57) ABSTRACT

A system and method which performs translumbosacral neuromodulation therapy in a subject by outputting pulses of magnetic energy onto the lumbar and sacral nerves of the subject is described. The system includes a control unit, an anorectal probe, at least one skin electrode, a first magnetic coil, a second magnetic coil, and a neurophysiological recorder. The control unit manages the system components. The anorectal probe and the skin electrode detect muscle activity when a nerve from the back of the subject is stimulated. The first magnetic coil outputs singular pulses of magnetic energy to localize a plurality of optimal stimulation sites. The second magnetic coil outputs repetitive pulses of magnetic energy to each of the plurality of optimal stimulation sites in order to treat medical problems. The neurophysiological recorder displays motor-evoked potential (MEP) data that is detected by the anorectal probe and the skin electrode through electromyographic sensors.

13 Claims, 14 Drawing Sheets

(56) References Cited

OTHER PUBLICATIONS

Rao SSC, Xiang X, Sharma A, Patcharatrakul T, Yan Y, Parr R, Ayyala D, Hamdy S. Neuromodulation Therapy for Fecal Incontinence: Randomized Frequency Response Trial.—Am J Gastroenterology 2020(In Press).

Rao SSC, Yan Y, Xiang X, Sharma A, Patcharatrakul T, Rattanakovit K, Ayyala D, Hamdy S. Effects of Translumbosacral Neuromodulation Therapy (TNT) on Gut and Brain Interactions and Anorectal Neuropathy in Fecal Incontinence (FI). Neurogastroenterol Motil 2019;31:Aug;111.

Rao SSC, Yan Y, Erdogan A, Mack A, Dewitt A, Sharma A. Translumbosacral Neuromodulation Therapy (TNT): A Novel Treatment for Levator ANI Syndrome (LAS). Gastroenterology 2020.

SYSTEM AND METHOD FOR PERFORMING TRANSLUMBOSACRAL NEUROMODULATION THERAPY IN A SUBJECT

The current application claims a priority to the U.S. Provisional Patent application Ser. No. 62/844,621 filed on May 7, 2019.

FIELD OF THE INVENTION

The present invention generally relates to systems and methods for non-invasive treatments of anorectal disorders, pelvic floor disorders, and other gastrointestinal motility disorders. More specifically, the present invention is a system and method for translumbosacral neuromodulation therapy that provides a new non-invasive treatment which uses magnetic energy primarily for the treatment of anorectal disorders such as fecal incontinence, anorectal pain, constipation and pelvic floor disorders as well as gastroparesis, Parkinson's disease, urinary incontinence, and back pain or bowel dysfunction after spinal cord injury.

BACKGROUND OF THE INVENTION

Anorectal disorders are common ailments which affect 15-20% of the population. There are limited treatment options for these conditions, and less than 40% of patients are satisfied with current treatment modalities. Commonly used therapies for fecal incontinence (FI) include antidiarrheal drugs (e.g. loperamide), surgical repair of torn anal sphincter muscles, or injection of sphincter bulking agents (e.g. NASHA dx) to create a protective barrier and biofeedback therapy. Each of these treatments correct only one of the myriad mechanisms that cause FI. An objective of the present invention is to describe Translumbosacral Neuromodulation Therapy (TNT), a novel treatment approach that uses magnetic energy for the treatment of neuropathy, muscle dysfunction, and sensory dysfunction in anorectal disorders.

TNT is a durable, efficacious, safe, mechanistically-based, non-invasive, and low risk treatment for anorectal disorders. Unlike existing treatments, TNT non-invasively targets the spinal nerve roots which regulate the anal and rectal muscles and sensation. Through the process of neuroplasticity, a phenomenon of enhancing growth and repair of damaged nerves and establishing new nerve connections, TNT produces a multidimensional effect on the anorectal muscles, nerves and sensation thereby improving FI. TNT significantly enhances the nerve signaling between the anorectum and the brain (afferent gut and brain connection) as well as the peripheral signaling between the spinal cord and anorectum (efferent). Thus, TNT produces bidirectional peripheral and central neuroplastic changes that impact nerve and muscle function.

SUMMARY OF THE INVENTION

Translumbosacral Neuromodulation Therapy (TNT) is a novel, non-invasive, low cost, low risk treatment that has a multidimensional therapeutic effect and is based on strong evidence of significant neuropathy to the anorectum and pelvic floor muscles in several anorectal disorders. Gastrointestinal neuropathy and lumbar nerves, thoracic nerves, sacral nerves, and vagal nerve neuropathy also occurs in patients with rectal hyposensitivity, constipation, urinary incontinence, patients with bowel dysfunction from spinal cord injury, Parkinson's disease, and gastroparesis. TNT capitalizes on the principle of neuroplasticity, i.e. the nervous system's ability to reorganize itself by forming new neural connections and improving connectivity. TNT builds on the concept of repetitive transcranial magnetic stimulation, a federal drug administration (FDA) approved treatment for depression where repetitive magnetic energy is applied to the brain. Here, we apply repetitive magnetic energy to stimulate the nerves in the back. TNT utilizes one or more magnetic coils to generate pulsed Electromagnetic Fields (EMFs) that penetrate 1-1.5 inches below the skin without causing irritation to other tissues and directly stimulate the nerves. The changing EMFs induce a flow of ions to generate and propagate electrical currents which depolarize or activate the nerves that induce contraction of muscle tissues. TNT further comprises novel parameters and modalities in order to apply repetitive magnetic energy to the peripheral thoracic, lumbar, and sacral spinal nerves. Further, TNT reverses the neuropathy in Fecal Incontinence (FI), rectal hyposensitivity, urinary incontinence, and anorectal pain syndromes especially levator ani syndrome, and the significant improvement in incontinence episodes, bowel function, and pelvic floor and anorectal pain correlates with improvement in neuropathy. Thus, TNT has important disease modifying neurobiological effects on the gut and its associated nervous system including the enteric nervous system.

DETAIL DESCRIPTIONS OF THE INVENTION

All illustrations of the drawings are for the purpose of describing selected versions of the present invention and are not intended to limit the scope of the present invention.

Figure 1:
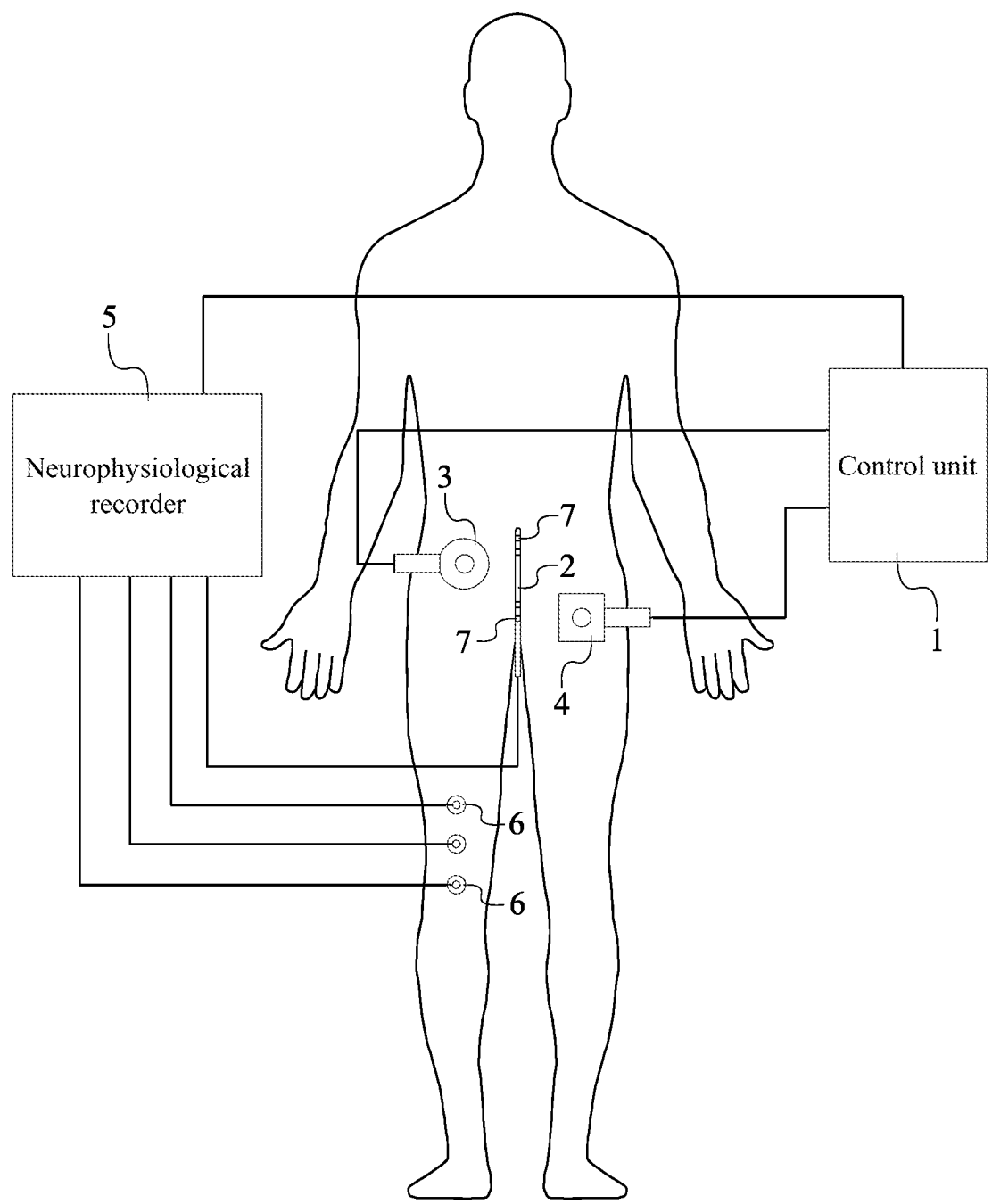
FIG. 1 is a schematic diagram illustrating the system of the present invention.

The present invention is a system and method for performing translumbosacral neuromodulation therapy in a subject. The present invention uses magnetic energy primarily for the treatment of disorders or conditions such as fecal incontinence, urinary incontinence, rectal hyposensitivity, constipation, irritable bowel syndrome, gastroparesis, Parkinson's disease, anorectal pain, spinal cord injury, bowel dysfunction, and pelvic floor disorders. In reference to FIG. 1, the system of the present invention includes a control unit 1, an anorectal probe 2, at least one skin electrode 6, a first magnetic coil 3, a second magnetic coil 4, and a neurophysiological recorder 5 (Step A). The control unit 1 is a magnetic stimulation device generates magnetic energy. The anorectal probe 2 and the skin electrode 6 detect muscle activity of a subject through electromyographic sensors. Preferably, more than one skin electrode 6 is used to detect muscle activity. The first magnetic coil 3 outputs singular pulses of magnetic energy generated from the control unit 1. The second magnetic coil 4 outputs repetitive pulses of magnetic energy generated from the control unit 1. The neurophysiological recorder 5 reads muscle activity data as motor-evoked potentials (MEPs) from the anus and rectum that is detected by the anorectal probe 2 and from the leg by the skin electrode 6. Further, the control unit 1 is communicably coupled to the first magnetic coil 3 and the second magnetic coil 4. Thus, magnetic energy managed by the control unit 1 can be outputted through the first magnetic coil 3 or the second magnetic coil 4. Moreover, the anorectal probe 2, the skin electrode 6, and the control unit 1 are communicably coupled to the neurophysiological recorder 5. Thus, the neurophysiological recorder 5 can display data that is detected by the anorectal probe 2 and the skin electrode 6, and the control unit 1 can manage data displayed by the neurophysiological recorder 5.

Figure 2:
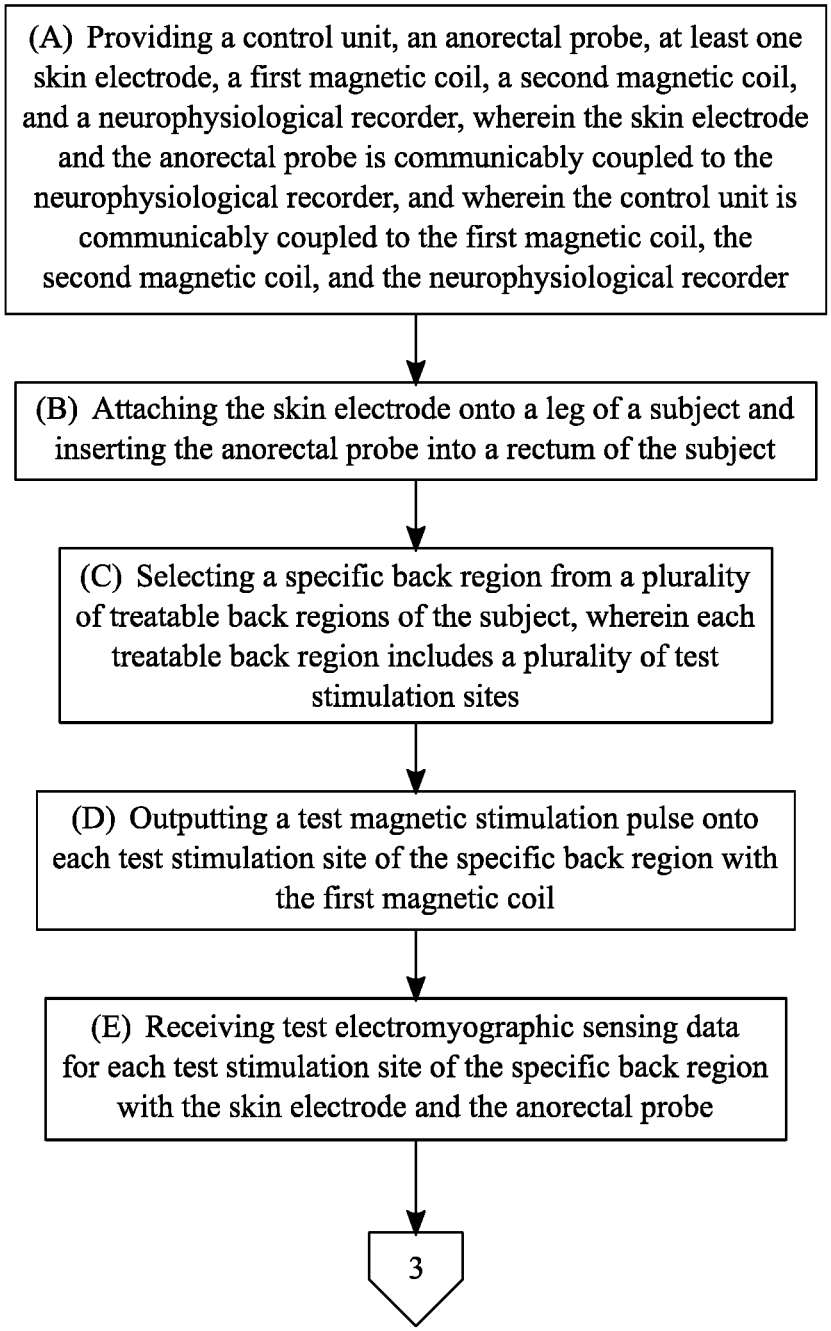
FIG. 2 is a flowchart illustrating the overall process for the method of the present invention.
Figure 3:
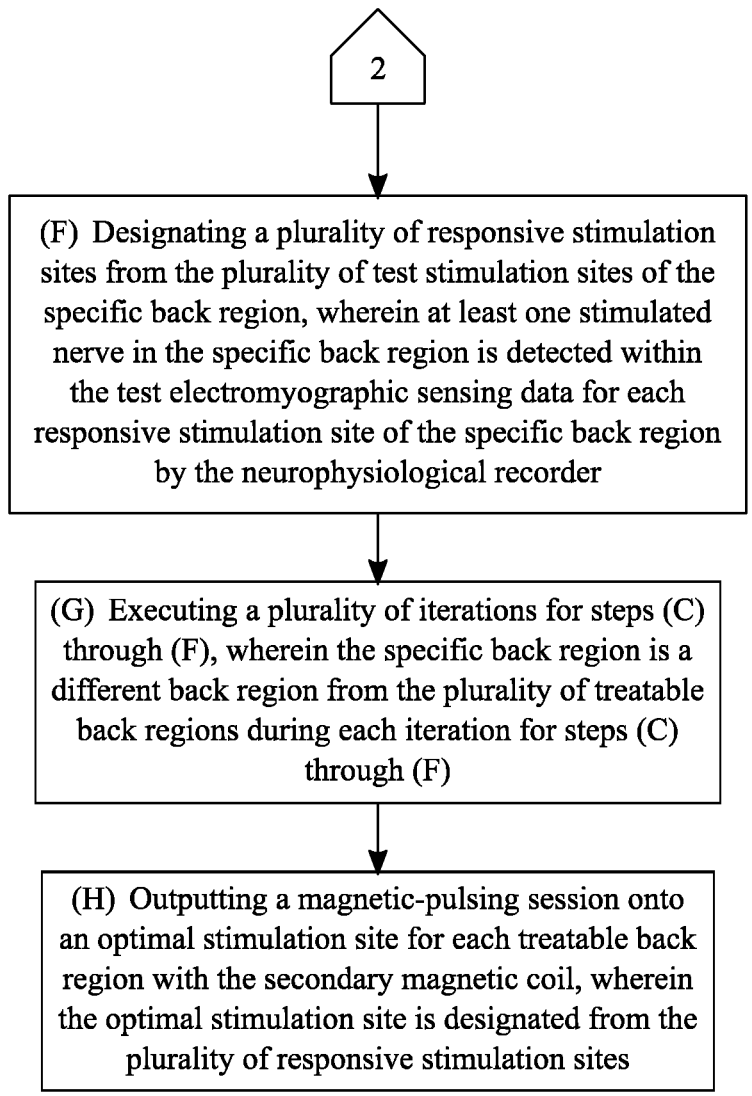
FIG. 3 is a flowchart illustrating a continuation of FIG. 2.

The method of the present invention follows an overall process that uses magnetic energy to perform translumbosacral neuromodulation therapy in a subject. In reference to FIGS. 2 and 3, the skin electrode 6 is attached to a leg of the subject, and the anorectal probe 2 is inserted into a rectum of the subject in order for the anorectal probe 2 and the skin electrode 6 to detect any electromyographic signals and MEPs indicating muscle activation (Step B). In further detail, the electromyographic sensors of the anorectal probe 2 are positioned within the anus and rectum of the subject in order for the anorectal probe 2 to precisely detect any MEPs from the subject's anorectum and in order for the skin electrode to detect any MEPs from the subject's leg. Further, the skin electrode 6 is attached to the subject's legs and buttocks before the anorectal probe 2 is inserted into the rectum of the subject. The anorectal probe 2 is additionally taped in place to maintain the anorectal probe 2 in position. A specific back region is selected from a plurality of treatable back regions of the subject, wherein each treatable back region includes a plurality of test stimulation sites (Step C). The plurality of treatable back regions is preferably at the thoracic, lumbar, and sacral regions of the subject. The specific back region is a particular thoracic, lumbar, or sacral region of the subject that is chosen by a medical professional. The plurality of test stimulation sites is a set of sites that are localized for treatment preparation of the subject. A test magnetic stimulation pulse is outputted onto each test stimulation site of the specific back region with the first magnetic coil 3 (Step D). The test magnetic stimulation pulse is a pulse of magnetic energy used to stimulate either lumbar or sacral nerves of the subject. Test electromyographic sensing data for each test stimulation site of the specific back region is received from the anorectal probe 2 (Step E). The test electromyographic sensing data is obtained when a muscle from the subject is excited and generates a MEP after stimulation of a selective lumbar, sacral, or thoracic nerve. A plurality of responsive stimulation sites is designated from the plurality of test stimulation sites of the specific back region, wherein at least one stimulated nerve in the specific back region is detected within the test electromyographic sensing data for each responsive stimulation site of the specific back region by the neurophysiological recorder 5 (Step F). The plurality of responsive stimulation sites may be designated by a medical professional after reading data from the neurophysiological recorder 5 or by the control unit 1. The plurality of responsive stimulation sites is a set of stimulation sites where a nerve is stimulated and, thus, muscle activity is detected. In further detail, each of the plurality of test stimulation sites is tested in order to identify if muscle activity is triggered at any of the plurality of test stimulation sites after receiving a pulse of magnetic energy. A plurality of iterations for Steps C through F is executed, wherein the specific back region is a different back region from the plurality of treatable back regions during each iteration for Steps C through F (Step G). In further detail, each test stimulation site of a corresponding treatable back region is tested in order to uniquely identify stimulation sites that trigger muscle activity within the subject. A magnetic-pulsing session is outputted onto an optimal stimulation site for each treatable back region with the second magnetic coil 4, wherein the optimal stimulation site is designated from the plurality of responsive stimulation sites (Step H). The optimal stimulation site is the stimulation site which triggered the highest muscle activity and MEP within the subject after receiving a pulse of magnetic energy. A magnetic-pulsing session is a session when repetitive magnetic energy pulses is outputted in order to perform translumbosacral neuromodulation therapy in the subject.

Figure 4:
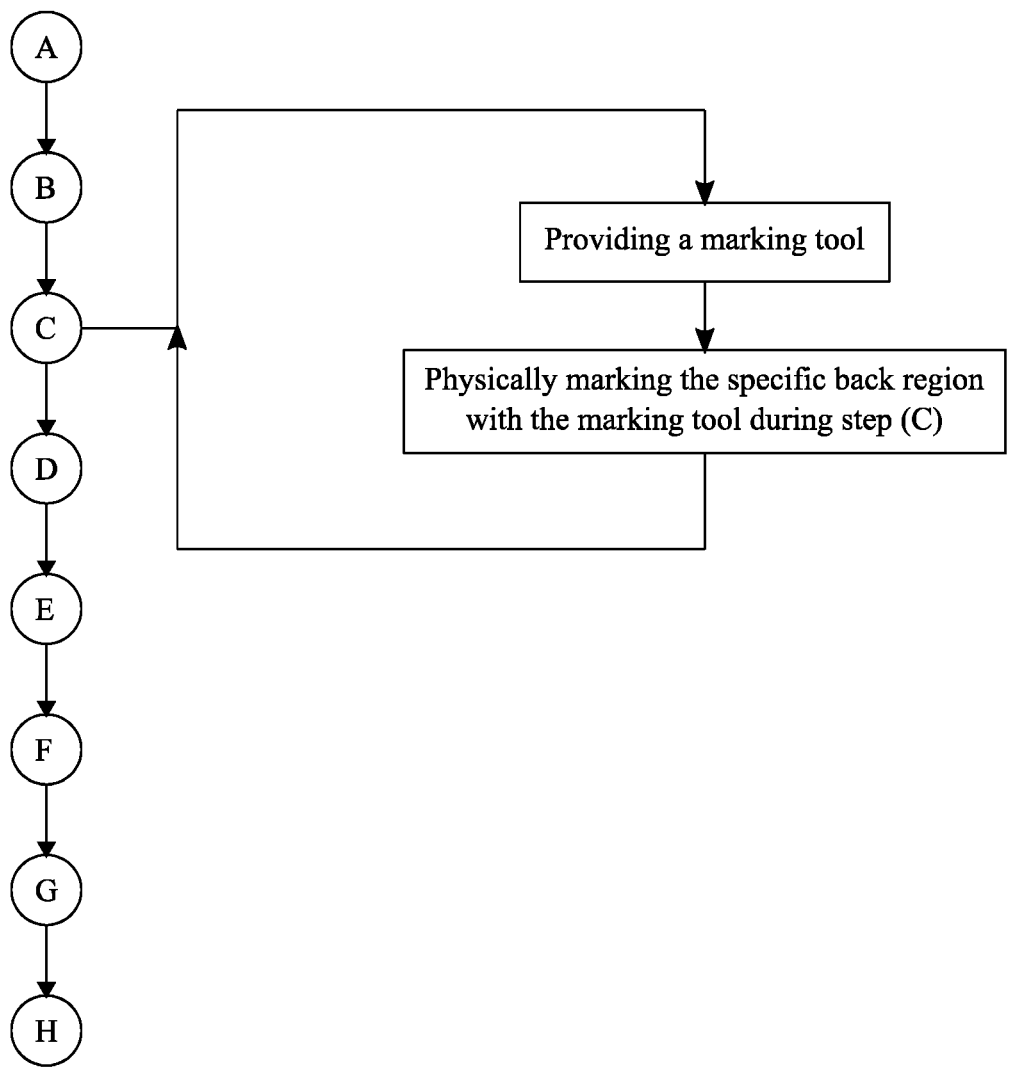
FIG. 4 is a flowchart illustrating the subprocess of marking the subject.

In order for a medical professional to better locate the optimal stimulation sites and with reference to FIG. 4, a marking tool is provided. The marking tool is preferably a marker. The specific back region is physically marked on the subject with the marking tool during Step C. In further detail, a medical professional marks where the lumbar and sacral nerves may be located based on anatomy with the marking tool. The medical professional also measures the distance between each marking in order to more accurately predict where the lumbar and sacral nerves may be located.

Figure 5:
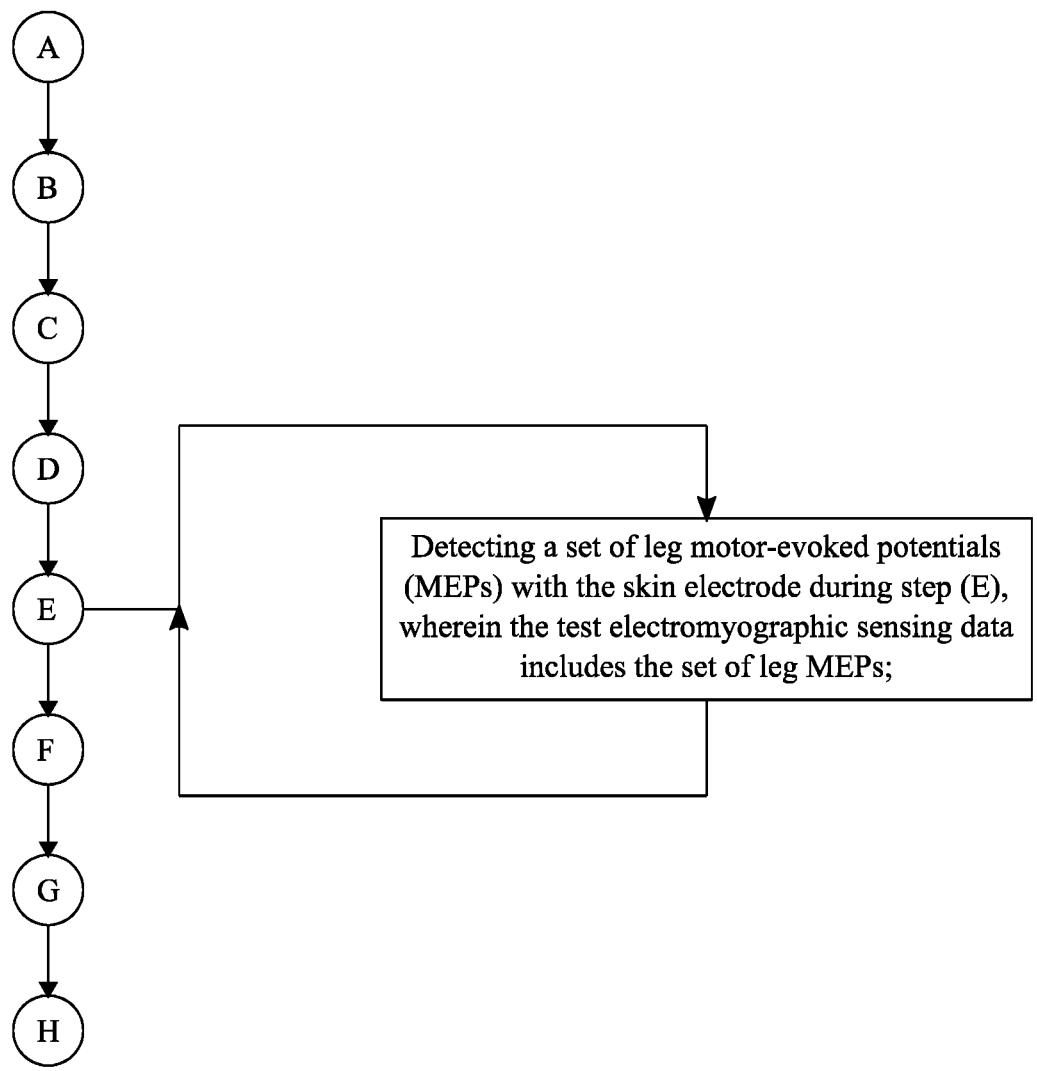
FIG. 5 is a flowchart illustrating the subprocess of obtaining of set of leg MEPs.

With reference to FIG. 5, the skin electrode 6 includes electromyographic sensors in order to externally detect muscle activity. More specifically, the skin electrode 6 detects a set of leg MEPs during Step E, wherein the test electromyographic sensors includes the set of leg MEPs. Thus, the skin electrode 6 can detect muscle activity of the subject's leg as the set of leg MEPs.

Figure 6:
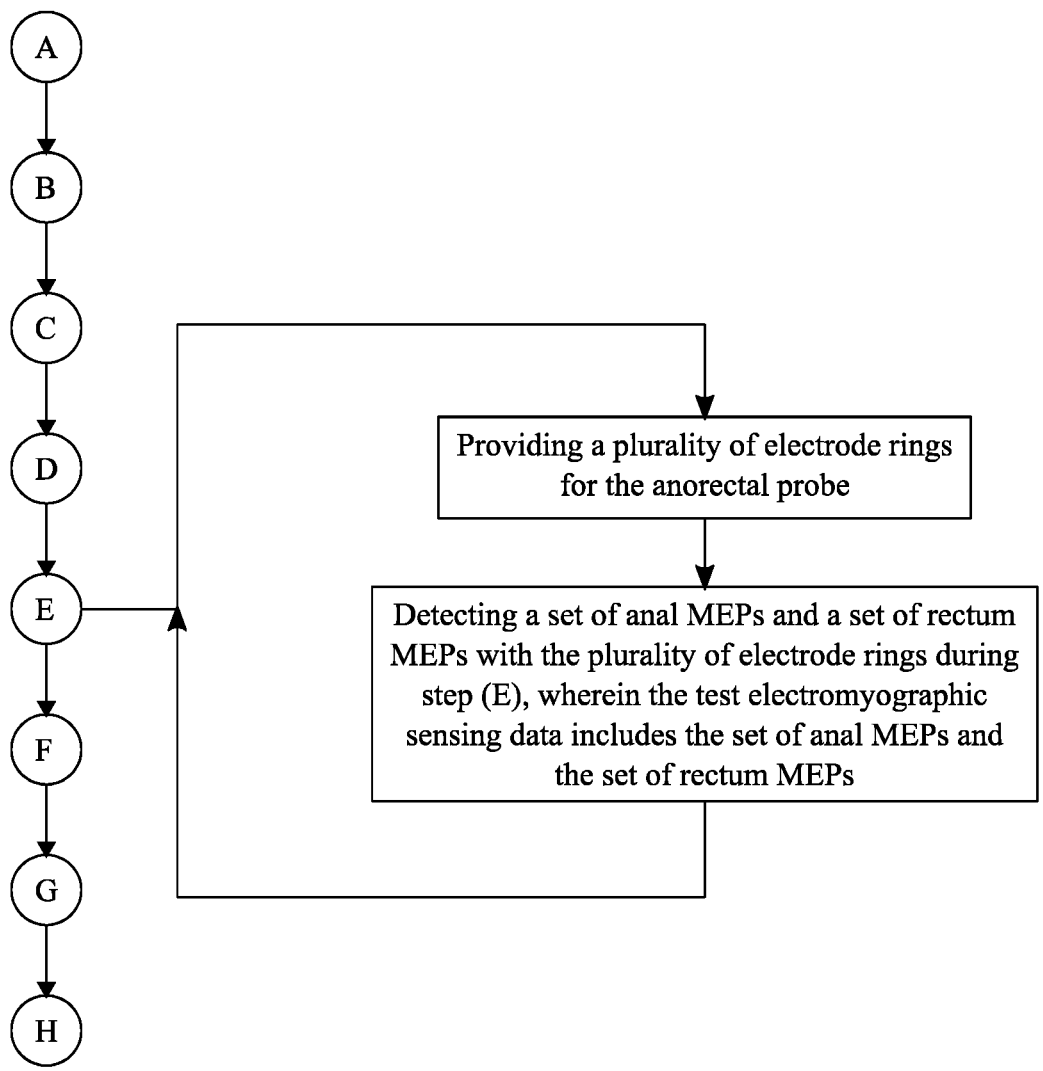
FIG. 6 is a flowchart illustrating the subprocess of obtaining a set of anal MEPs and a set of rectum MEPs.

In order for the anorectal probe 2 to able to internally detect muscle activity and with reference to FIG. 6, a plurality of electrode rings 7 is provided for the anorectal probe 2. The plurality of electrode rings 7 is a set of electromyographic sensors. Moreover, the plurality of electrode is preferably a set of four steel rings that is distributed along the anorectal probe 2. A set of anal MEPs and a set of rectum MEPs are detected with the plurality of electrode rings 7 during Step E. The set of anal MEPs indicates the muscle activity detected in the anus of the subject, and the set of rectum MEPs indicates the muscle activity detected in the rectum of the subject. The test electromyographic sensing data includes the set of anal MEPs and the set of rectum MEPs. Thus, the anorectal probe 2 can detect muscle activity of the subject's anorectum through the plurality of electrode rings 7.

Figure 7:
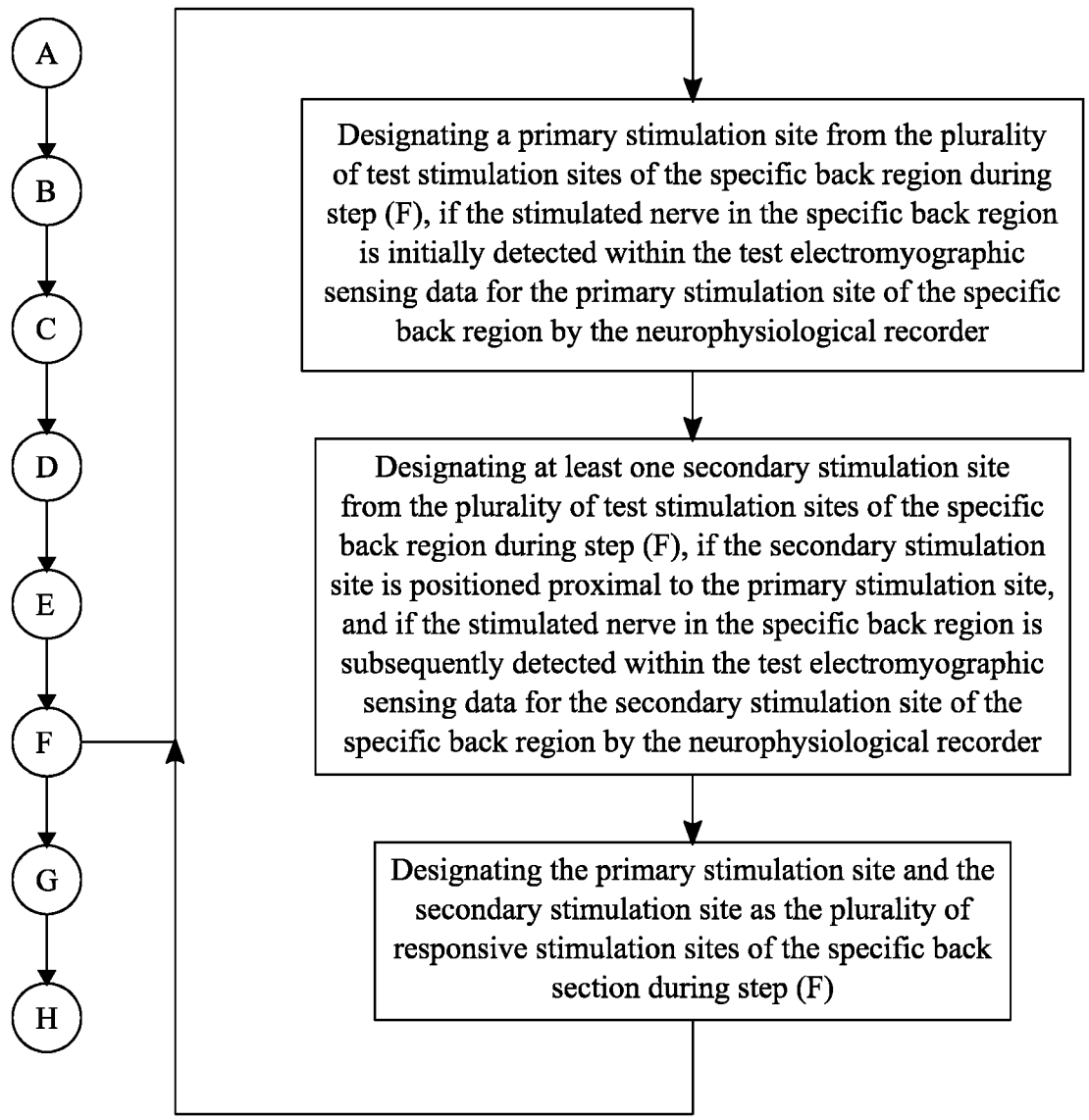
FIG. 7 is a flowchart illustrating the subprocess of determining the primary and secondary stimulation sites.

With reference to FIG. 7, the following subprocess is used to identify the plurality of responsive stimulation sites for each treatable back region. A primary stimulation site is designated from the plurality of test stimulation sites of the specific back region during Step F, if the stimulated nerve in the specific back region is initially detected within the test electromyographic sensing data for the primary stimulation site of the specific back region by the neurophysiological recorder 5. The primary stimulation site may be designated by a medical professional after reading data from the neurophysiological recorder 5 or by the control unit 1. Further, the primary stimulation site is preferably the first stimulation site where a notable amount of muscle activity is detected by a MEP reading. At least one secondary stimulation site is designated from the plurality of test stimulation sites of the specific back region during Step F, if the secondary stimulation site is positioned proximal to the primary stimulation site, and if the stimulated nerve in the specific back region is subsequently detected within the test electromyographic sensing data for the secondary stimulation site of the specific back region by the neurophysiological recorder 5. The secondary stimulation site may be designated by a medical professional after reading data from the neurophysiological recorder 5 or by the control unit 1. Further, the secondary stimulation site is preferably a stimulation site adjacent to the primary stimulation site, typically within a 1-inch to 2-inch radius around the primary stimulation site. The primary stimulation site and the secondary stimulation site is designated as the plurality of responsive stimulation sites of the specific back region during Step F. Thus, the plurality of responsive stimulation sites for each treatable back region is identified.

Figure 8:
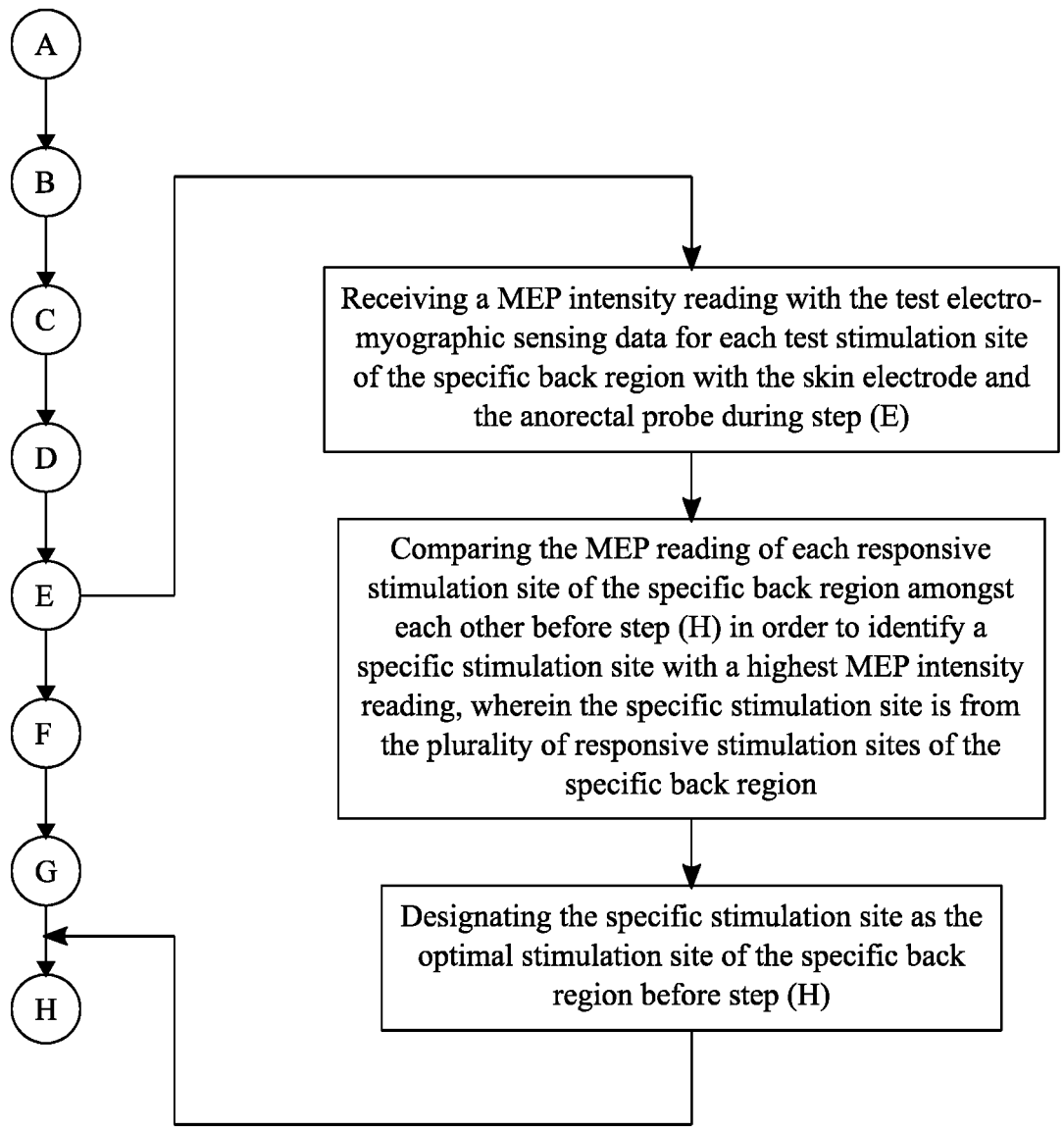
FIG. 8 is a flowchart illustrating the subprocess of finding the optimal stimulation site for each treatable back region.
Figure 14:
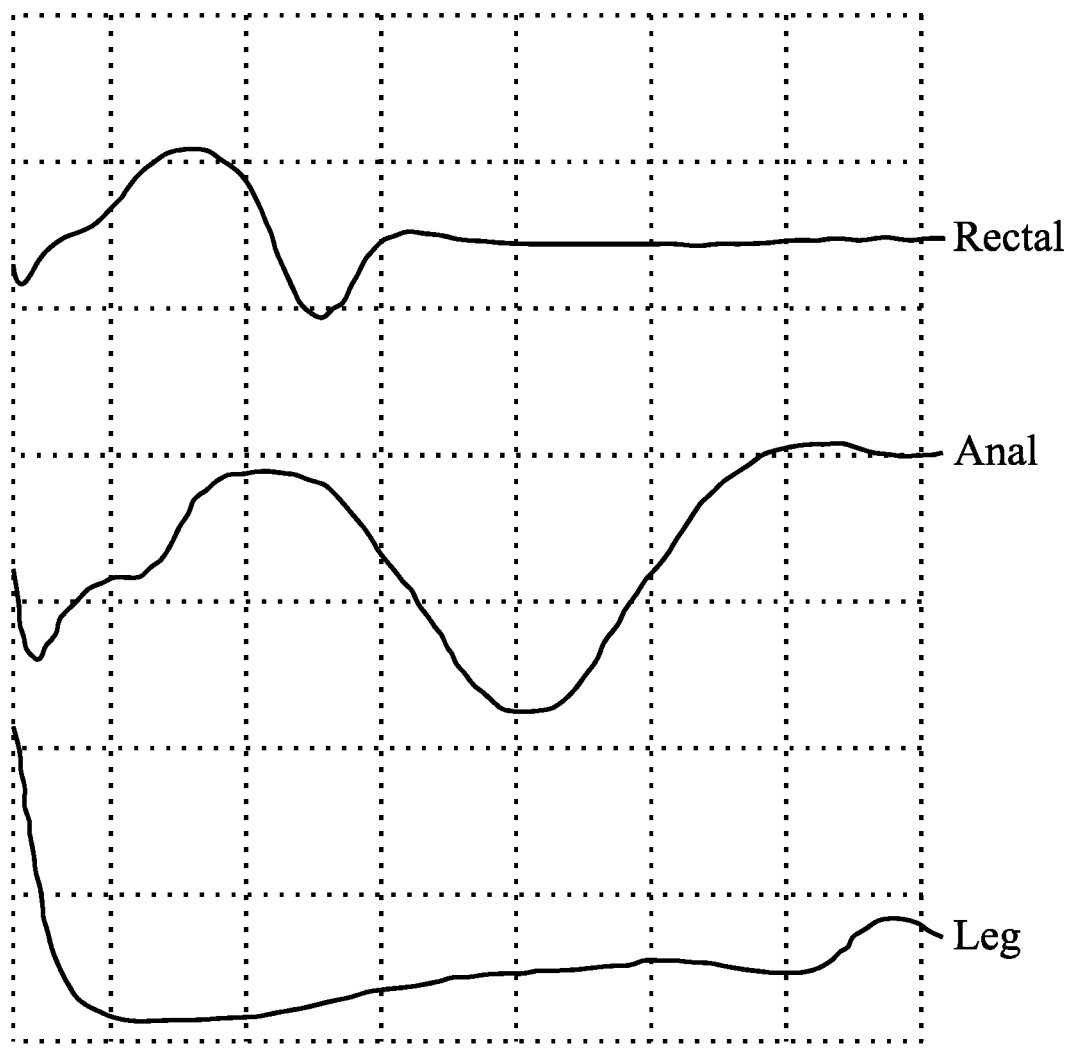
FIG. 14 is an example graph illustrating a comparison between an anal MEP, a rectum MEP, and a leg MEP.

With reference to FIG. 8, the following subprocess is used to identify the optimal stimulation site for each treatable back region. A MEP intensity reading is received with the test electromyographic sensing data for each test stimulation site of the specific back region with the skin electrode 6 and the anorectal probe 2 during Step E. The MEP intensity reading is data that illustrates the intensity of the triggered muscle activity within the subject after a nerve is stimulated. The MEP intensity reading of each responsive stimulation site of the specific back region is compared amongst each other before Step H in order to identify a specific stimulation site with a highest MEP intensity reading, wherein the specific stimulation site form the plurality of responsive stimulation sites of the specific back region. In further detail and with reference to FIG. 14, a MEP graph is generated which illustrates the MEP intensity at each responsive stimulation site of the specific back region. The responsive stimulation site, where the highest MEP intensity was detected, is identified as the specific stimulation site by a medical professional or the control unit 1. The specific stimulation site is designated as the optimal stimulation site of the specific back region before Step H. Thus, the optimal stimulation site is identified for each treatable back region.

Figure 9:
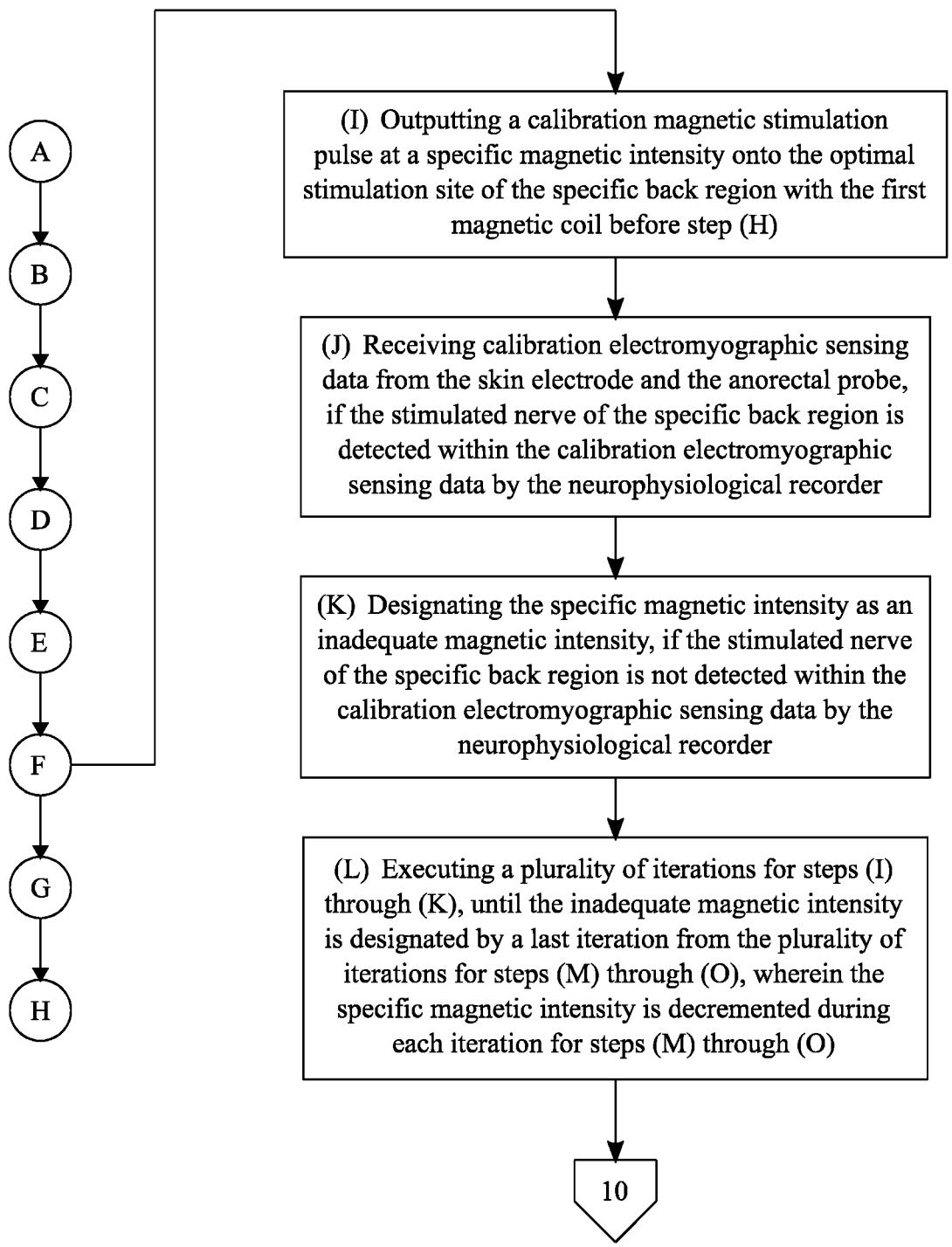
FIG. 9 is a flowchart illustrating the subprocess of finding the threshold magnetic intensity at each optimal stimulation site.
Figure 10:
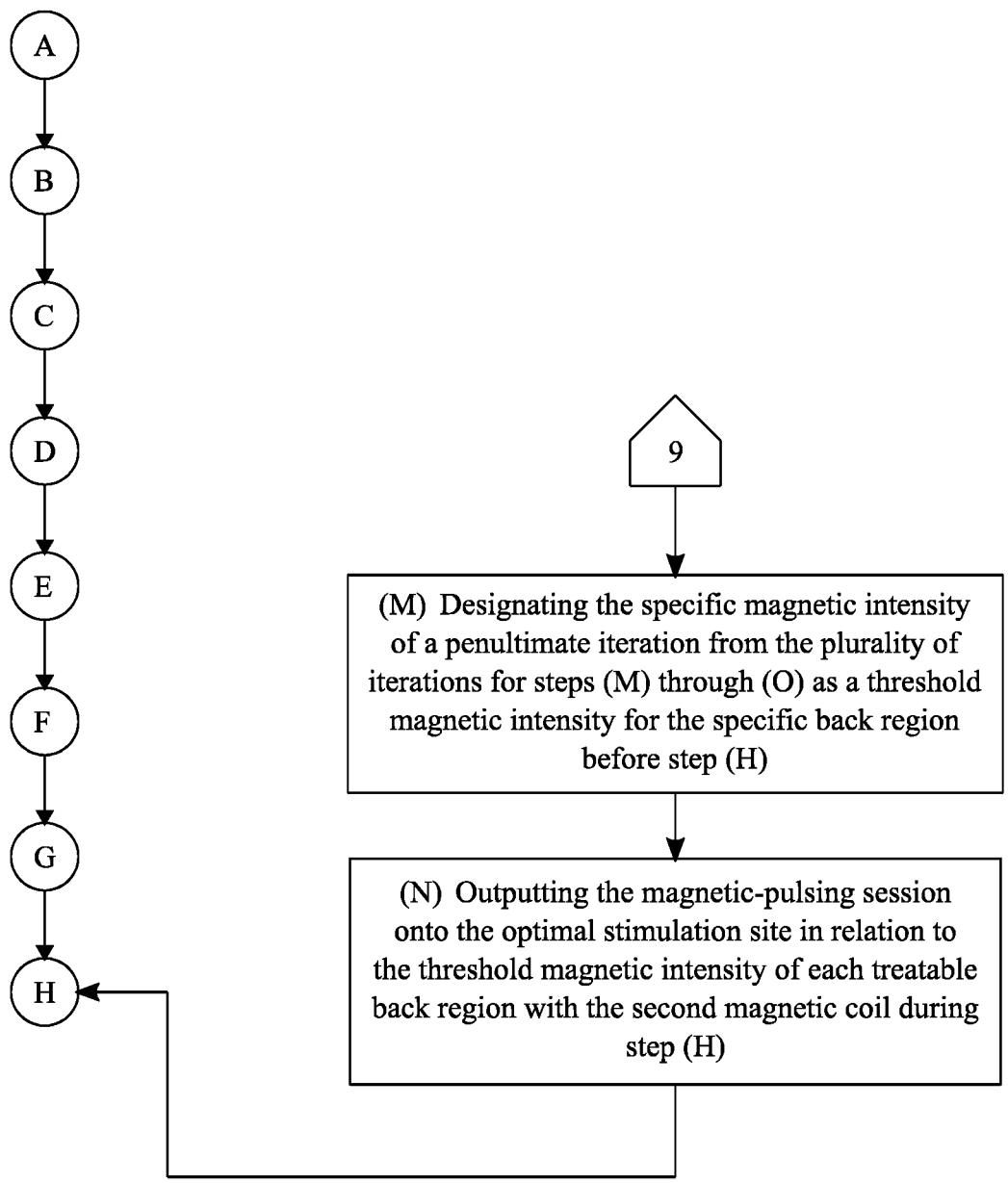
FIG. 10 is a flowchart illustrating a continuation of FIG. 9.

In order to stimulate the nerves with optimal intensity of magnetic energy and to prevent harm to the subject during the translumbosacral neuromodulation therapy and with reference to FIGS. 9 and 10, a threshold magnetic intensity is identified before the subject is treated by the second magnetic coil 4. The threshold magnetic intensity is the minimum magnetic energy intensity that can be applied to the subject in order to trigger a muscle contraction. The following subprocess allows the threshold magnetic intensity to be identified. A calibration magnetic stimulation pulse is outputted at a specific magnetic intensity onto the optimal stimulation site with the first magnetic coil 3 before Step H (Step I). The calibration magnetic stimulation pulse is a singular pulse of magnetic energy, and the specific magnetic intensity is an initial magnetic energy level that is predetermined by clinical trials. Calibration electromyographic sensing data is received from the skin electrode 6 and the anorectal probe 2 if the initial stimulated nerve is detected within the calibration electromyographic sensing data by the neurophysiological recorder 5 (Step J). In further detail, the medical professional can read the calibration electromyographic sensing data in order to determine that the calibration magnetic stimulation pulse at the specific magnetic intensity is enough to trigger muscle activity or a MEP within the subject. The specific magnetic intensity is designated as an inadequate magnetic intensity with the control unit 1 if the initial stimulated nerve is not detected within the calibrated electromyographic sensing data by the neurophysiological recorder 5 (Step K). The inadequate magnetic intensity is a magnetic energy level too low to trigger muscle activity or a MEP within the subject. A plurality of iterations for Steps M through O is executed, until the inadequate magnetic intensity is designated by the control unit 1 by a last iteration from the plurality of iterations for Steps M through O, wherein the specific magnetic intensity is decremented during each iteration for Steps M through O (Step L). In further detail, the magnetic energy intensity level managed by the control unit 1 is lowered in stepwise increments, typically 1% to 2%, in order to identify the lowest magnetic energy intensity required to trigger muscle activity within the subject. The specific magnetic intensity of a penultimate iteration from the plurality of iterations for Steps M through O is designated as the threshold magnetic intensity for the specific back region (Step M). The penultimate iteration is the iteration of the lowest magnetic energy intensity that is able to trigger muscle activity or a MEP within the subject. Thus, the minimum magnetic energy intensity is relayed to the medical professional in order safely treat the subject. The magnetic-pulsing session is outputted onto the optimal stimulation site of each treatable back region in relation to the threshold magnetic intensity with the second magnetic coil 4 during Step H (Step R). Thus, the translumbosacral neuromodulation therapy is safely performed in the subject.

Figure 11:
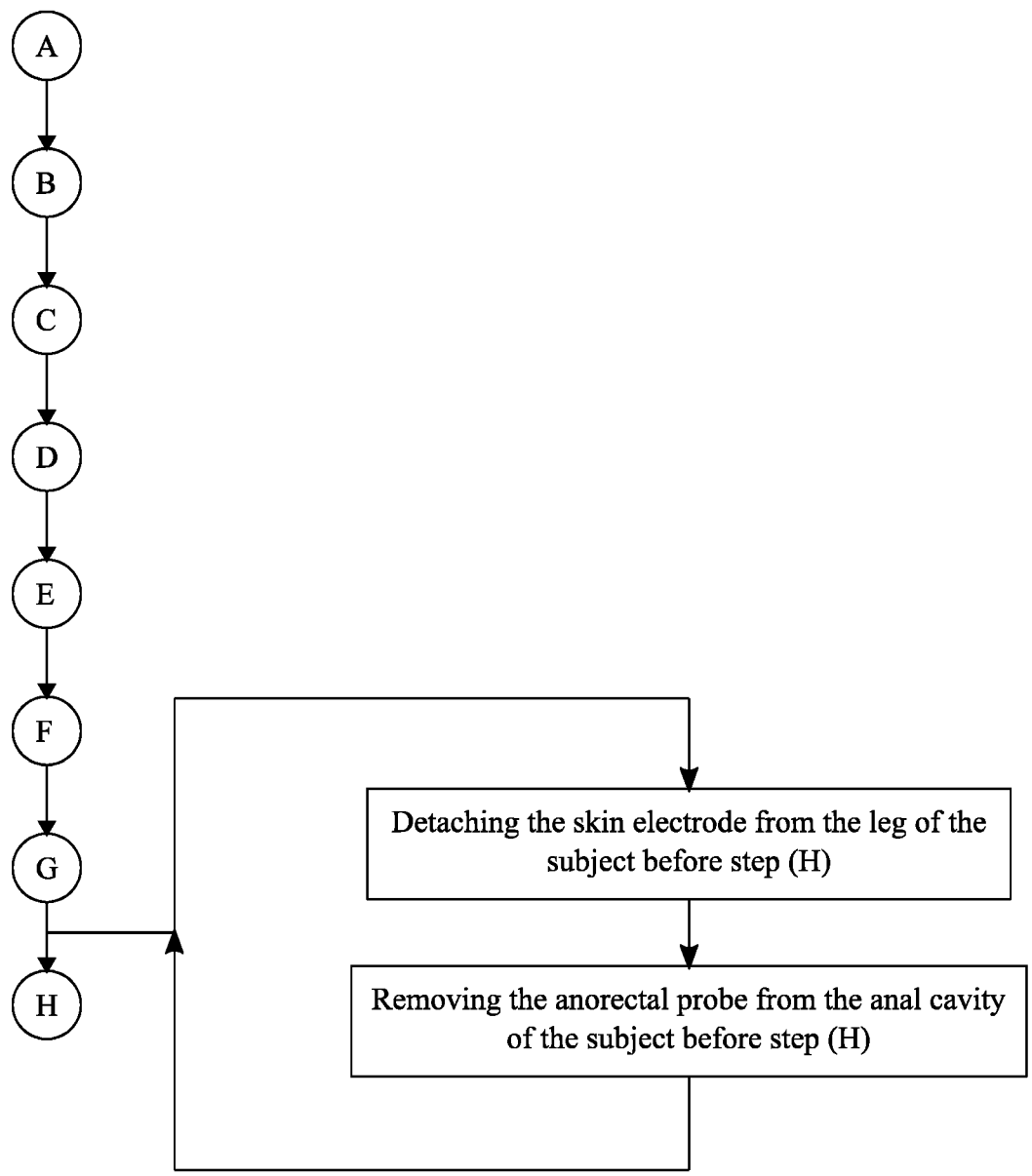
FIG. 11 is a flowchart illustrating the subprocess of detaching the skin electrode and removing the anorectal probe.

After the plurality of optimal sites are localized and the threshold magnetic intensity is found and with reference to FIG. 11, the skin electrode 6 can be detached from the leg of the subject, and the anorectal probe 2 can be removed from the rectum of the subject before Step H. MEPs are not measured during treatment of the subject. Thus, the anorectal probe 2 and the skin electrode 6 are removed in order for the patient to be more comfortable during the translumbosacral neuromodulation therapy.

Figure 12:
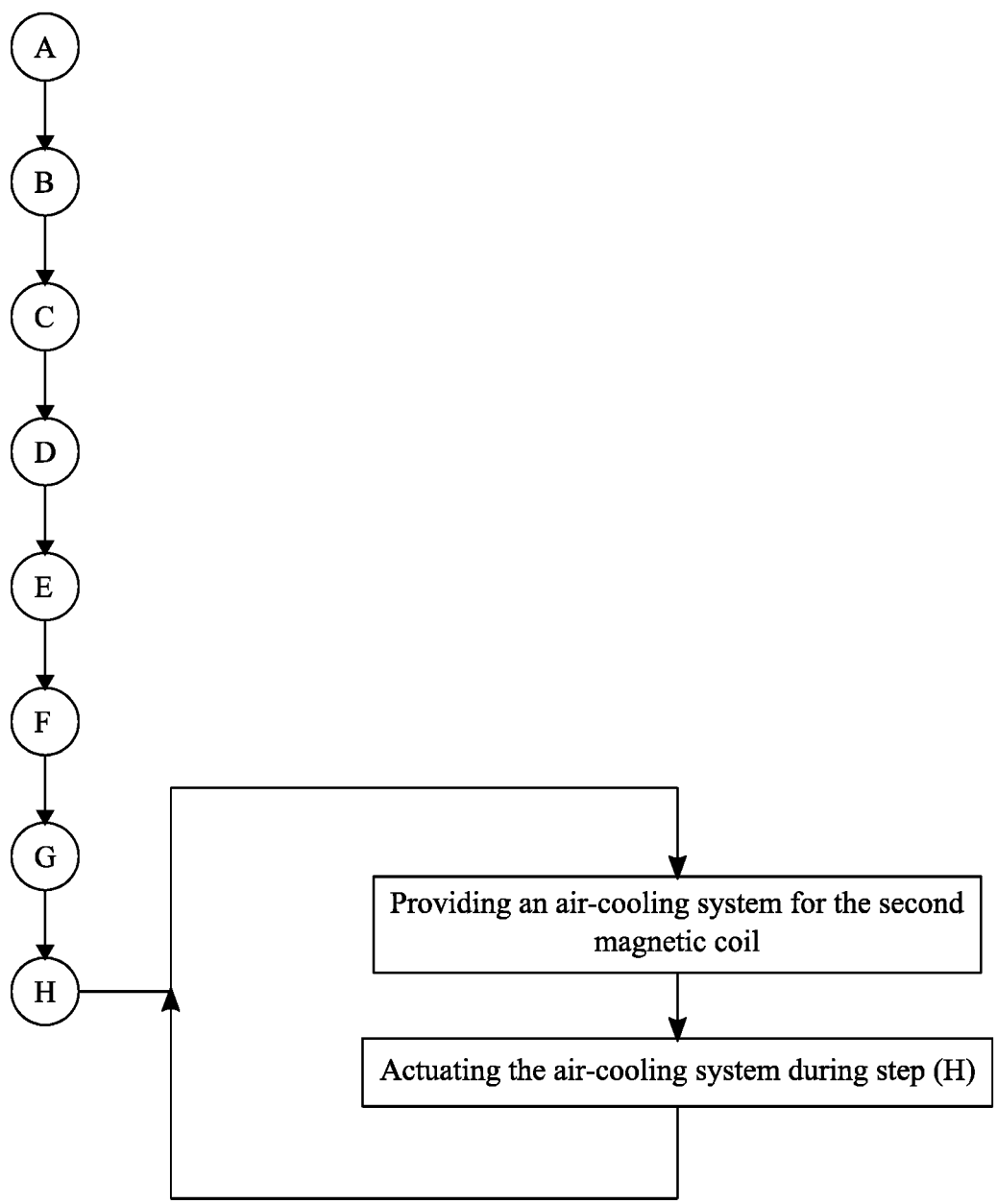
FIG. 12 is a flowchart illustrating the subprocess of air-cooling the second magnetic coil.

In order to prevent the second magnetic coil 4 from overheating and with reference to FIG. 12, an air-cooling system is provided for the second magnetic coil 4. The air-cooling system is a safety measure that prevents overheating of the second magnetic coil 4 and, thus, prevents accidently causing a burn on the subject. Additionally, there is a preventative mechanism built-in the second magnetic coil 4 that automatically causes the second magnetic coil 4 to stop firing when it reaches high temperatures to prevent accidental burning of the subject. The air-cooling system is actuated during Step H in order to prevent overheating of the second magnetic coil 4.

In order to modify the treatment accordingly for a subject, parameters for the plurality of magnetic-pulsing sessions can be adjusted. One parameter that can be adjusted is an output percentage of the threshold magnetic intensity percentage.

Figure 13:
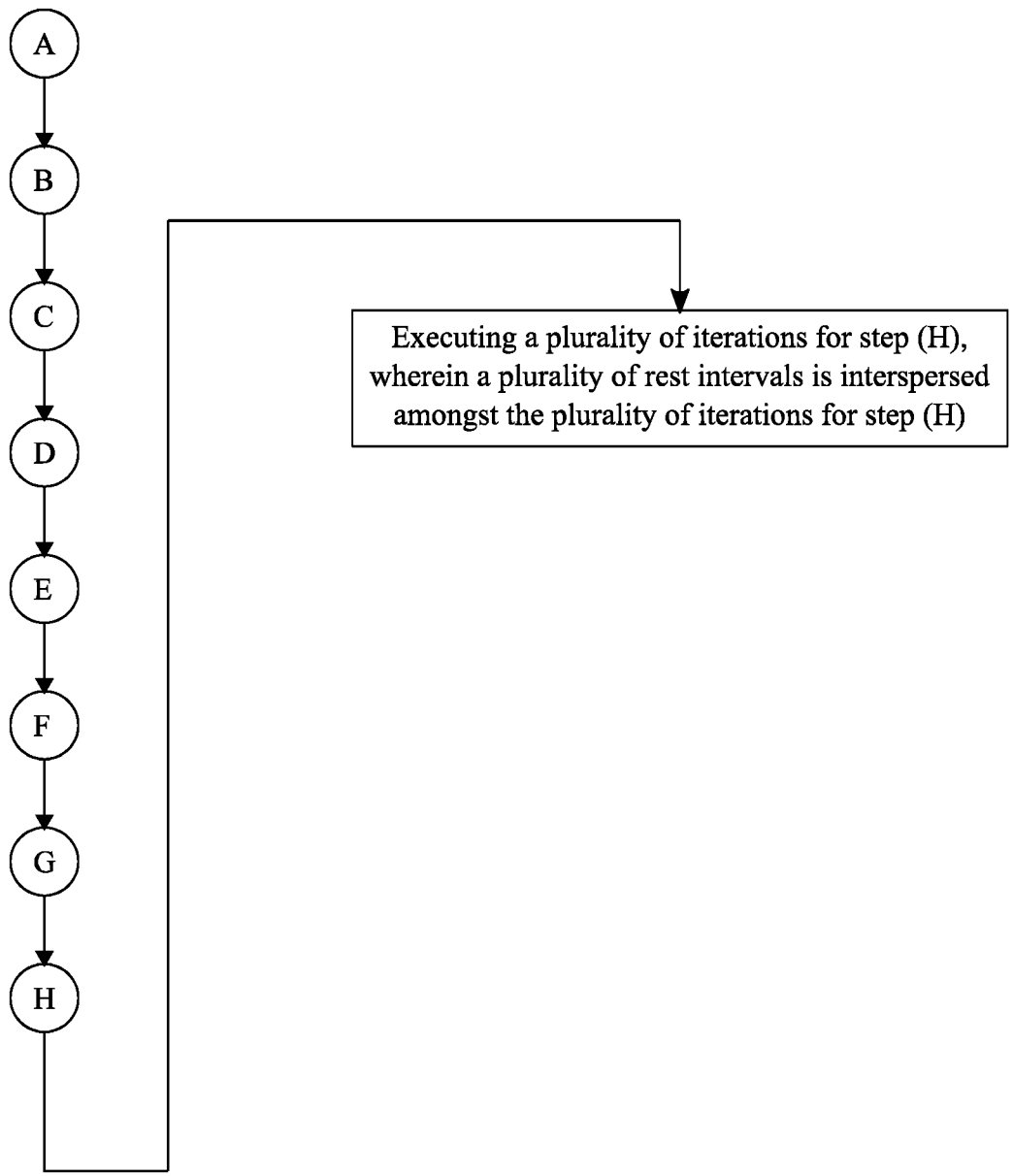
FIG. 13 is a flowchart illustrating the subprocess of repeating treatments for each treatable back region.

For example, the magnetic-pulsing session can be outputted at a range between 10% to 50% of the threshold magnetic intensity. This specific range of threshold magnetic intensity is defined as the minimum motor threshold. Another parameter that can be adjusted is the frequency of each magnetic-pulsing session. For example, the magnetic-pulsing session can be outputted between a frequency range of 1 Hertz (Hz) to 20 Hz with the second magnetic coil 4 during Step H. This specific range of frequencies is predetermined through clinical trials. Another parameter that can be adjusted is the total number of pulses that are outputted during a magnetic-pulsing session. For example, the magnetic-pulsing session is within a range of 300 magnetic pulses to 3600 magnetic pulses. This specific range of magnetic pulses is also predetermined through clinical trials. Furthermore and with reference to FIG. 13, a plurality of iterations for Step H is executed, wherein a plurality of rest intervals is interspersed amongst the plurality of iterations for Step H. Thus, the optimal stimulation site of each treatable back region can be treated multiple times, and each of the plurality of rest intervals is the amount of resting time in between one magnetic-pulsing session of treatment and the next magnetic-pulsing session of treatment. For example, the optimal stimulation site of each treatable back region can be treated 2-30 times at a duration range between 5 seconds to 20 minutes.

Clinical Trials

In a randomized dose-ranging trial, the plausibility and optimal frequency of a novel neuromodulation therapy by administering repetitive Translumbar Magnetic Stimulation (rTLMS) and Transsacral Magnetic Stimulation (rTSMS) in patients with FI. FI patients were randomized to receive weekly (greater than or equal to one episode per week) rTLMS and rTSMS treatments with either one Hertz, five Hertz, or 15 Hertz, over six weeks. Two trains of 300 stimulations each were given at four sites, a total of 2400 pulses, by applying transcutaneous magnetic stimulation via a focal coil to the lumbar and sacral regions. Daily fecal incontinence (FI) episodes and bowel symptoms were assessed with prospective stool diaries and compared before and after treatment. FI severity index (FISI) and subject's global assessment (SGA) were also compared. Patients with greater than or equal to 50 percent decrease in weekly FI episodes were considered responders.

In this preliminary report of the trial, twenty-six FI patients, 18 females and eight males, participated. Nine patients were randomized to one Hertz, eight to five Hertz, and nine to 15 Hertz, respectively. The weekly FI episodes decreased significantly in the one Hertz (p=0.004) and 15 Hertz group (p=0.023), but not in the five Hertz group (p=0.281) when compared to baseline. However, there was no difference between groups (p=0.170). There was a significant difference between responder rates (p=0.024) with the one Hertz group showing a significantly higher responder rate (88.9%) than the five Hertz group (25%), but not between other groups. After treatment, the FISI score increased by 34.6±55.3% in the one Hertz group, 12.0±13.9% in the five Hertz group, and 17.6±48.2% in the 15 Hertz group, but there was no difference between groups (p=0.652). Complete or considerable improvement in FI symptoms was reported by 66.7% of patients in the one Hertz group, 37.5% in the five Hertz group, and 44.4% in the 15 Hertz group (p=0.480). One patient had numbness/tingling in the right arm in the 5 Hertz group. In conclusion, this interim analysis shows repetitive Trans-lumbar and Trans-sacral magnetic stimulations appear safe, and at one Hertz frequency showed significant superiority when compared to five Hertz and 15 Hertz, respectively, for the treatment of FI. TNT modality offers promise as a novel treatment approach for FI.

In this final report of the trial, thirty-three FI patients, 21 females and 12 males were randomized to one Hertz, five Hertz, and 15 Hertz respectively with 11 patients in each group. No baseline demographic, symptomatic, and neuropathic differences. The one Hertz group showed significantly higher responder rate when compared to the five Hertz group (p=0.02) or the 15 Hertz group (p=0.04). However, there was no difference between the five Hertz group and the 15 Hertz group (p=0.6). The weekly FI episodes decreased significantly in the one Hertz group (p=0.01), the five Hertz group, and the 15 Hertz group (p=0.007) when compared to baseline. After treatment, both the SGA score and FISS score decreased significantly in the one Hertz (p=0.02) group, with only SGA in the 15 Hertz group and FISS in the five Hertz group. Two patients had transient numbness/tingling and two had unrelated serious adverse events. The squeeze pressure and maximum tolerable volume increased significantly (p<0.03), and anal neuropathy normalized, indicating mechanistic improvement in the one Hertz group. The fecal incontinence quality of life significantly improved in most domains with one Hertz and five Hertz but was inconsistent in the 15 Hertz group. In conclusion, TNT at one Hertz frequency was superior and showed greatest therapeutic promise for FI when compared to five Hertz and 15 Hertz. FI symptoms, anorectal physiology, neuropathy, and quality of life improved significantly demonstrating both symptomatic and mechanistic improvement. Additional studies revealed that 1 hertz frequency improved ano-cortical and recto-cortical evoked potentials indicating improved communication between the anorectum and brain. These mechanistic underpinnings provide evidence that TNT improves bowel function through neuroplasticity. A recent study also showed that TNT improves anorectal and pelvic floor pain in levator ani syndrome.

Although the invention has been explained in relation to its preferred embodiment, it is to be understood that many other possible modifications and variations can be made without departing from the spirit and scope of the invention as hereinafter claimed.

What is claimed is:

1. A method for performing translumbosacral neuromodulation therapy in a subject, the method comprises the steps of:
 (A) providing a control unit, an anorectal probe, at least one skin electrode, a first magnetic coil, a second magnetic coil, and a neurophysiological recorder, wherein the skin electrode and the anorectal probe is communicably coupled to the neurophysiological recorder, and wherein the control unit is communicably coupled to the first magnetic coil, the second magnetic coil, and the neurophysiological reader;
 (B) attaching the skin electrode onto a leg of the a subject and inserting the anorectal probe into a rectum of the subject;
 (C) selecting a specific back region from a plurality of treatable back regions of the subject, wherein each treatable back region includes a plurality of test stimulation sites;
 (D) outputting a test magnetic stimulation pulse onto each test stimulation site of the specific back region with the first magnetic coil;
 (E) receiving test electromyographic sensing data for each test stimulation site of the specific back region with the anorectal probe and the skin electrode;

(F) designating a plurality of responsive stimulation sites from the plurality of test stimulation sites of the specific back region, wherein at least one stimulated nerve in the specific back region is detected within the test electromyographic sensing data for each responsive stimulation site of the specific back region by the neurophysiological recorder;

(G) executing a plurality of iterations for steps (C) through (F), wherein the specific back region is a different back region from the plurality of treatable back regions during each iteration for steps (C) through (F); and (H) outputting a magnetic-pulsing session onto an optimal stimulation site for each treatable back region with the second magnetic coil, wherein the optimal stimulation site is designated from the plurality of responsive stimulation sites.

2. The method for performing translumbosacral neuromodulation therapy in a subject as claimed in claim 1, the method comprises the steps of:
providing a marking tool; and
physically marking the specific back region with the marking tool during step (C).

3. The method for performing translumbosacral neuromodulation therapy in a subject as claimed in claim 1, the method comprises the step of:
detecting a set of leg motor-evoked potentials (MEPs) with the skin electrode during step (E), wherein the test electromyographic sensing data includes the set of leg MEPs.

4. The method for performing translumbosacral neuromodulation therapy in a subject as claimed in claim 1, the method comprises the steps of:
providing a plurality of electrode rings for the anorectal probe; and
detecting a set of anal MEPs and a set of rectum MEPs with the plurality of electrode rings during step (E), wherein the test electromyographic sensing data includes the set of anal MEPs and the set of rectum MEPs.

5. The method for performing translumbosacral neuromodulation therapy in a subject as claimed in claim 1, the method comprises the steps of:
designating a primary stimulation site from the plurality of test stimulation sites of the specific back region during step (F), if the stimulated nerve in the specific back region is initially detected within the test electromyographic sensing data for the primary stimulation site of the specific back region by the neurophysiological recorder;
designating at least one secondary stimulation site from the plurality of test stimulation sites of the specific back region during step (F), if the secondary stimulation site is positioned proximal to the primary stimulation site, and if the stimulated nerve in the specific back region is subsequently detected within the test electromyographic sensing data for the secondary stimulation site of the specific back region by the neurophysiological recorder; and
designating the primary stimulation site and the secondary stimulation site as the plurality of responsive stimulation sites of the specific back section during step (F).

6. The method for performing translumbosacral neuromodulation therapy in a subject as claimed in claim 1, the method comprises the steps of:
receiving a MEP intensity reading with the test electromyographic sensing data for each test stimulation site of the specific back region with the skin electrode and the anorectal probe during step (E);
comparing the MEP reading of each responsive stimulation site of the specific back region amongst each other before step (H) in order to identify a specific stimulation site with a highest MEP intensity reading, wherein the specific stimulation site is from the plurality of responsive stimulation sites of the specific back region;
designating the specific stimulation site as the optimal stimulation site of the specific back region before step (H).

7. The method for performing translumbosacral neuromodulation therapy in a subject as claimed in claim 1, the method comprises the steps of:
(I) outputting a calibration magnetic stimulation pulse at a specific magnetic intensity onto the optimal stimulation site of the specific back region with the first magnetic coil before step (H);
(J) receiving calibration electromyographic sensing data from the skin electrode and the anorectal probe, if the stimulated nerve of the specific back region is detected within the calibration electromyographic sensing data by the neurophysiological recorder;
(K) designating the specific magnetic intensity as an inadequate magnetic intensity, if the stimulated nerve of the specific back region is not detected within the calibration electromyographic sensing data by the neurophysiological recorder;
(L) executing a plurality of iterations for steps (I) through (K), until the inadequate magnetic intensity is designated by a last iteration from the plurality of iterations for steps (M) through (O), wherein the specific magnetic intensity is decremented during each iteration for steps (M) through (O);
(M) designating the specific magnetic intensity of a penultimate iteration from the plurality of iterations for steps (M) through (O) as a threshold magnetic intensity for the specific back region before step (H); and
(N) outputting the magnetic-pulsing session onto the optimal stimulation site in relation to the threshold magnetic intensity of each treatable back region with the second magnetic coil during step (H).

8. The method for performing translumbosacral neuromodulation therapy in a subject as claimed in claim 7, wherein the magnetic-pulsing session is outputted at a range between 10% to 50% of the threshold magnetic intensity.

9. The method for performing translumbosacral neuromodulation therapy in a subject as claimed in claim 1, the method comprises the steps of:
detaching the skin electrode from the leg of the subject before step (H); and
removing the anorectal probe from the anal cavity of the subject before step (H).

10. The method for performing translumbosacral neuromodulation therapy in a subject as claimed in claim 1, the method comprises the steps of:
providing an air-cooling system for the second magnetic coil; and
actuating the air-cooling system during step (H).

11. The method for performing translumbosacral neuromodulation therapy in a subject as claimed in claim 1, wherein the magnetic-pulsing session is within a frequency range of 1 Hertz (Hz) to 20 Hz.

12. The method for performing translumbosacral neuromodulation therapy in a subject as claimed in claim 1, wherein the magnetic-pulsing session is within a range of 300 magnetic pulses to 3600 magnetic pulses.

13. The method for performing translumbosacral neuromodulation therapy in a subject as claimed in claim 1, the method comprises the step of:

executing a plurality of iterations for step (H), wherein a plurality of rest intervals is interspersed amongst the plurality of iterations for step (H).

* * * * *